(12) United States Patent
Mosadegh et al.

(10) Patent No.: US 10,548,745 B2
(45) Date of Patent: Feb. 4, 2020

(54) PORTABLE PROSTHETIC HAND WITH SOFT PNEUMATIC FINGERS

(71) Applicant: President and Fellows of Harvard College, Cambridge, MA (US)

(72) Inventors: Bobak Mosadegh, New York, NY (US); Brandon Grant Gerberich, Wilbraham, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/632,952

(22) Filed: Jun. 26, 2017

(65) Prior Publication Data

US 2017/0290681 A1    Oct. 12, 2017

Related U.S. Application Data

(63) Continuation of application No. 14/685,126, filed on Apr. 13, 2015, now Pat. No. 9,687,362.

(Continued)

(51) Int. Cl.
*A61F 2/54* (2006.01)
*A61F 2/74* (2006.01)
(Continued)

(52) U.S. Cl.
CPC .............. *A61F 2/586* (2013.01); *A61F 2/583* (2013.01); *A61F 2/68* (2013.01); *A61F 2/72* (2013.01);
(Continued)

(58) Field of Classification Search
CPC .... A61F 2/586; A61F 2/588; A61F 2002/587; B25J 15/0023; B25J 15/12; B25J 9/142; F15B 15/103
See application file for complete search history.

(56) References Cited

U.S. PATENT DOCUMENTS 4,784,042 A    11/1988 Paynter
5,568,957 A    10/1996 Haugs
(Continued)

FOREIGN PATENT DOCUMENTS

EP    1190819 A1    3/2002
WO    WO 90/15696 A1 * 12/1990 .............. B25J 15/00
(Continued)

OTHER PUBLICATIONS

Brown, E., et al., Universal robotic gripper based on the jamming of granular material. Proceedings of the National Academy of Sciences, 2010, 5 pages.
(Continued)

*Primary Examiner* — David H Willse
(74) *Attorney, Agent, or Firm* — Wilmer Cutler Pickering Hale and Dorr LLP

(57) ABSTRACT

A finger actuator, includes a plurality of fluidically interconnected inflatable chambers, wherein each chamber comprises outer walls having an embedded extensible layer selected to constrain radial expansion and freestanding inner walls; and an inextensible layer connected to the chambers at a base of the chambers, the inextensible layer comprising a flexible polymer and having an embedded inextensible layer that extends along the length of the finger actuator.

17 Claims, 11 Drawing Sheets

Related U.S. Application Data

(60) Provisional application No. 61/978,412, filed on Apr. 11, 2014.

(51) Int. Cl.

| | | |
|---|---|---|
| *B25J 15/12* | (2006.01) | |
| *A61F 2/58* | (2006.01) | |
| *B29C 70/88* | (2006.01) | |
| *B29C 70/54* | (2006.01) | |
| *B29C 70/70* | (2006.01) | |
| *B25J 15/00* | (2006.01) | |
| *A61F 2/68* | (2006.01) | |
| *A61F 2/72* | (2006.01) | |
| *F15B 15/10* | (2006.01) | |
| *B25J 9/14* | (2006.01) | |
| *B29L 31/00* | (2006.01) | |
| *A61F 2/50* | (2006.01) | |

(52) U.S. Cl.
CPC ............ *B25J 9/142* (2013.01); *B25J 15/0023* (2013.01); *B25J 15/12* (2013.01); *B29C 70/541* (2013.01); *B29C 70/70* (2013.01); *B29C 70/88* (2013.01); *F15B 15/103* (2013.01); *A61F 2/5044* (2013.01); *A61F 2002/5012* (2013.01); *A61F 2002/5039* (2013.01); *A61F 2002/5056* (2013.01); *A61F 2002/74* (2013.01); *A61F 2002/747* (2013.01); *A61F 2002/748* (2013.01); *B29L 2031/7532* (2013.01)

(56) References Cited

U.S. PATENT DOCUMENTS

| | | | |
|---|---|---|---|
| 6,178,872 | B1 | 1/2001 | Schulz |
| 9,687,362 | B2 * | 6/2017 | Mosadegh .............. B25J 15/12 |
| 2002/0157388 | A1 | 10/2002 | Seto et al. |
| 2003/0110938 | A1 | 6/2003 | Seto et al. |
| 2006/0028041 | A1 | 2/2006 | Ono et al. |
| 2007/0199399 | A1 | 8/2007 | Okazaki et al. |
| 2012/0216672 | A1 | 8/2012 | Menon et al. |
| 2015/0266186 | A1 | 9/2015 | Mosadegh et al. |

FOREIGN PATENT DOCUMENTS

| | | | |
|---|---|---|---|
| WO | WO-2012/148472 A2 | 11/2012 | |
| WO | WO 2012/159737 A1 * | 11/2012 | ............ B25J 9/142 |
| WO | WO-2013/110086 A1 | 7/2013 | |

OTHER PUBLICATIONS

Chou, C.P. and B. Hannaford, Measurement and modeling of McKibben pneumatic artificial muscles. IEEE Transactions on Robotics and Automation, 1996. 12(1): p. 90-102.

European Search Report issued European application No. 15776043. 0, dated Oct. 20, 2017, 13 pages.

Ilievski, F., et al., Soft robotics for chemists. Angew Chem Int Ed Engl, 2011. 50(8): p. 1890-5.

International Search Report and Written Opinion issued by the European Patent Office as International Searching Authority for International Application No. PCT/US2013/066164 dated Jun. 4, 2014 (12 pages).

International Search Report and Written Opinion issued by the U. S. Patent and Trademark Office as International Searching Authority for International Application No. PCT/US2015/025561 dated Jul. 9, 2015 (9 pages).

International Search Report and Written Opinion dated Apr. 16, 2015, in the International application No. PCT/US14/51818, filed Aug. 20, 2014, 13 pages.

Kim, M.S., et al., Manufacturing of inchworm robot using shape memory alloy (SMA) embedded composite structure. International Journal of Precision Engineering and Manufacturing, 2011. 12(3): p. 565-568.

Lee, H., C.G. Xia, and N.X. Fang, First jump of microgel; actuation speed enhancement by elastic instability. Soft Matter, 2010. 6(18): p. 4342-4345.

Martinez, R.V., et al., Elastomeric Origami: Programmable Paper-Elastomer Composites as Pneumatic Actuators. Advanced Functional Materials, 2012. 22(7): p. 1376-1384.

Martinez, R.V., et al., Robotic tentacles with three-dimensional mobility based on flexible elastomers. Adv Mater, 2013. 25(2): p. 205-12.

Morin, S.A., et al., Camouflage and display for soft machines. Science, vol. 337, No. 6096, Aug. 17, 2012, pp. 828-832.

Otake, M., et al., Motion design of a starfish-shaped gel robot made of electro-active polymer gel. Robotics and Autonomous Systems, 2002. 40(2-3): p. 185-191.

Polygerinos, P. et al., "Towards a Soft Pneumatic Glove for Hand Rehabilitation," Intelligent Robots and Systems (IROS), 2013 IEEE/RSJ International Conference, pp. 1512-1517 (Nov. 2013).

Shepherd, R.F., et al., Multigait soft robot. Proc Natl Acad Sci U S A, 2011. 108(51): p. 20400-3.

Shepherd, R.F., et al., Using Explosions to Power a Soft Robot. Angew Chem Int Ed Engl, vol. 52, pp. 2892-2896, 2013.

Shi, L.W., et al., A Novel Soft Biomimetic Microrobot with Two Motion Attitudes. Sensors, 2012. 12(12): p. 16732-16758.

Wakimoto, S., K. Suzumori, and K. Ogura, Miniature Pneumatic Curling Rubber Actuator Generating Bidirectional Motion with One Air-Supply Tube. Advanced Robotics, 2011. 25(9-10): p. 1311-1330.

* cited by examiner

PORTABLE PROSTHETIC HAND WITH SOFT PNEUMATIC FINGERS

CROSS-REFERENCE(S) TO RELATED APPLICATIONS

The present application is a continuation application of and claims the benefit of priority to U.S. application Ser. No. 14/685,126, filed Apr. 13, 2015, now U.S. Pat. No. 9,687,362, which claims the benefit of U.S. patent application Ser. No. 61/978,412 filed on Apr. 11, 2014, the content of which are hereby incorporated by reference herein in their entirety.

TECHNICAL FIELD

This technology relates generally to prosthetic devices. In particular, this invention relates to a hand prosthesis including soft pneumatic fingers.

BACKGROUND

There are over one half million people with upper limb amputations in the United States as of 2014. The options for prosthetic devices include (a) passive/cosmetic devices that are ascetically appealing, but which provide little functionality, and (b) active/robotic devices that can assist with some natural motions. Despite the clear advantages of an active/robotic device, only a third of those patients who might benefit actually use an active prosthesis. While robotic prosthesis can provide strength and motor control, the high cost and weight serves as an impediment to its adoption.

A prosthesis device using light weight actuation methods that can be readily incorporated into prosthetic devices is needed.

SUMMARY

The invention provides an actuator, acuator fabrication and design useful in manufacture of prosthesis with soft components.

The prosthesis components include 1) fingers which are pneumatic/hydraulic actuators that bend when filled with pressurized gas/liquid from compressors/pumps located in the housing of the hand, and 2) a control system which uses the compressors/pumps to pressurize the fingers.

In one aspect, a finger actuator includes a plurality of fluidically interconnected extensible segments separated from adjacent extensible segments by a flexible, inextensible hinge, wherein the extensible segments comprise at least one fluidically interconnected inflatable chamber, and the extensible segments comprise an outer wall selected to constrain radial expansion and a freestanding inner wall; and an inextensible layer connected to the extensible segments at a base of the extensible segments, the inextensible layer comprising a flexible polymer and having an embedded inextensible layer that extends along the length of the finger actuator.

In one or more embodiments, the plurality of extensible segments includes 3-6 segments.

In any preceding embodiment, at least one extensible segment includes two fluidically interconnected chambers, and for example, the at least one extensible segment has two inner walls at opposing ends of the segmentand the two fluidically interconnected chambers are located proximate to the inner walls.

In any preceding embodiment, the flexible, inextensible hinge is integral with the inextensible layer.

In any preceding embodiment, the outer wall selected to constrain radial expansion comprises an embedded extensible layer.

In any preceding embodiment, the extensible segments are made of a silicone rubber.

In any preceding embodiment, the extensible fabric includes spandex fabric, polyamide, or elastane.

In any preceding embodiment, the embedded inextensible layer includes cotton, paper, or polyester layers.

In any preceding embodiment, the inextensible layer is made of the same material as the extensible segments, or the inextensible layer is made of a different material than the extensible segments.

In any preceding embodiment, the chambers are molded.

In one aspect a prosthetic hand includes a base and a plurality of finger actuators according to any embodiment described herein.

In one or more embodiments, the prosthetic hand further includes at least one air compressor coupled for pressurization of at least one finger actuator.

In one or more embodiments, the prosthetic hand further includes at least one valve for reversibly coupling the air compressor to at least one finger actuator.

In any preceding embodiment, the prosthetic hand further includes a microprocessor for receiving input from a sensor capable of reading muscle voltage.

In any preceding embodiment, the microprocessor provides instructions to the valve in response to a signal received from the sensor.

In another aspect, a method of operating a prosthetic hand includes providing a prosthetic hand according to any embodiment described herein; and providing instructions to the valve to open, wherein air pressure from the air compressor pressurizes at least one finger actuator, thereby causing the finger actuator to bend.

In one or more embodiments, the instruction is in response to a signal received from the sensor.

In another aspect, a method of making a finger actuator includes introducing an elastic reinforcement layer into each of a plurality of mold chambers; positioning a lost wax member along the length of the mold and spanning across each of the mold chambers; filling the mold with an elastomeric material and curing the elastomeric material; before during or after curing the elastomeric material, providing an inextensible layer to the base of the mold chambers; and after curing the elastomeric material, heating the cured finger actuator to melt the lost wax member.

These and other aspects and embodiments of the disclosure are illustrated and described below.

It is contemplated that any embodiment disclosed herein may be properly combined with any other embodiment disclosed herein. The combination of any two or more embodiments disclosed herein is expressly contemplated.

BRIEF DESCRIPTION OF THE DRAWING

The invention is described with reference to the following figures, which are presented for the purpose of illustration only and are not intended to be limiting.

In the Drawings.

DETAILED DESCRIPTION

Figure 1:
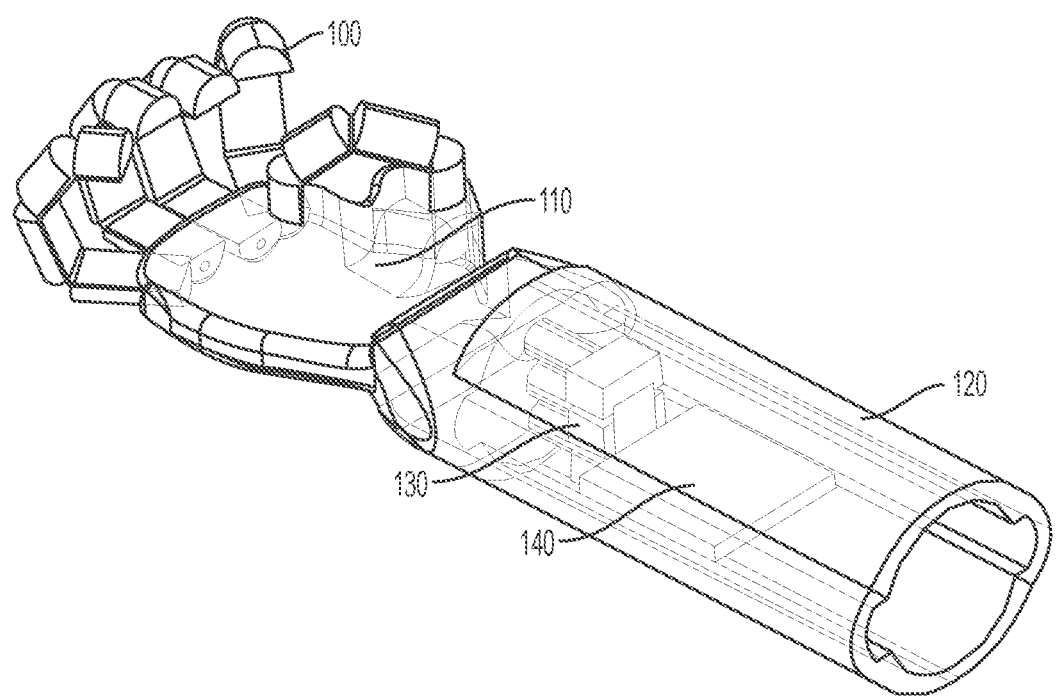
FIG. 1 is a schematic representation of a hand prosthesis having soft pneumatically activated fingers according to one or more embodiments.

A prosthesis device using light weight actuators that can be readily incorporated into prosthetic devices is described. FIG. 1 is a schematic illustration of a prosthetic device for a hand according to one or more embodiments. The prosthesis includes soft fluidically, e.g., pneumatically, activated actuators 100 ("finger actuators") that are integrated into a base 110. The soft actuators are configured to actuate for gripping such as a three-point grip, i.e. a grip imitating the one achieved by a natural hand when the thumb, index and long fingers grip an object. The base can be attached to a sleeve 120 that can accommodate the base and permit a turning or swiveling motion that approximates wrist movement. The sleeve can house air compressors 130 for actuation of the soft actuators and a battery power source 140 to run the compressors. Compressors/pumps are used to inflate the actuators. Optionally, some or all of the processing components can be housed in the base.

Finger Actuators

The actuator includes an extensible elastomeric top layer bonded to an inextensible bottom layer. The inextensible layer can include a flexible polymer that has a restraining element, such as paper or mesh, embedded in the layer.

The actuators employ an extensible fabric to increase the toughness of the elastomer used for the fingers. Since most compressors are limited in their output pressure, the actuators according to one or more embodiments maximize their exerted forces at lower pressures. To achieve this, soft elastomers, which require less stress to achieve a given strain, as compared to stiff elastomers, are reinforced using an extensible fabric. By reinforcing the soft elastomer, the effective toughness of the actuator increases (e.g., withstands larger pressures) and therefore exerts higher forces. The extensible fabric can either be in the form of a woven mesh (e.g., spandex, polyester-polyurethane copolymers or other combinations of elastic polymer meshes (e.g., silicone, polyurethane, polyamide, elastane)).

Both the upper extensible portion and the lower inextensible layer includes flexible polymers, and can include for example elastomers. The elastomeric layer can be made using conventional elastomeric polymers, such as silicone rubber. Elastomers with low stiffness will provide larger amplitude of motion for a given pressure, as compared to stiffer elastomers. Stiffer elastomers, however, will provide a larger range of forces (before bursting due to overpressurization).

Figure 2A:
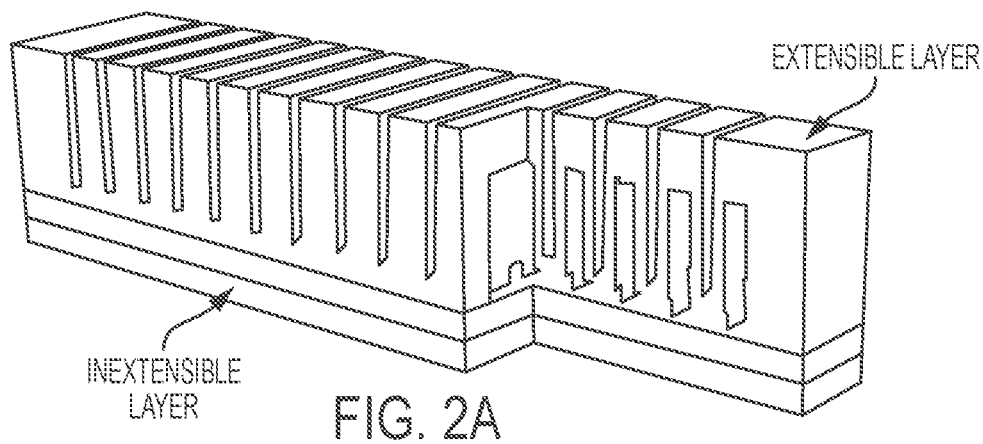
FIGS. 2A and 2B are perspective and cross-sectional illustrations, respectively, of a finger actuator according to one or more embodiments.
Figure 2B:
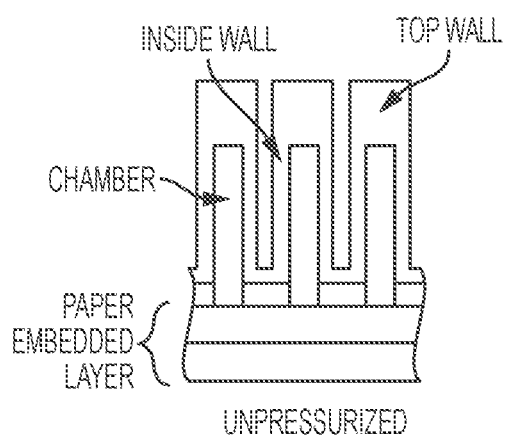
Figure 2C:
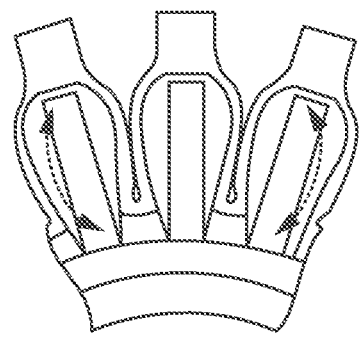
FIG. 2C is a cross-sectional schematic illustration of actuation of a finger actuator according to one or more embodiments.

The extensible top layer consists of inflatable chambers that allow the actuator to bend when pressurized. The bending motion results from a difference in elasticity between the elastomeric materials used for the inflatable chambers and an internally-embedded inelastic fabric located near the bottom of the actuator. FIG. 2 illustrates the components and mode of actuation of the finger actuator. FIG. 2A provides a perspective view of the finger actuator design having a plurality of chambers, each of which can function as a finger joint, secured to an inextensible base. FIG. 2B is a cross-sectional view of the actuator showing the individual chambers, with free side walls, and secured to a inelastic, e.g., reinforcing sheet embedded, layer. FIG. 2C illustrates the mechanism of actuation. Pressure (gas or liquid) expands the chambers, which are prevented from radial expansion due to the inextensible layer and the thicker outer walls that prevent radial expansion. Expansion therefore occurs in the lateral direction and bending occurs. While shown here for chambers having flat sides, it is contemplated that the actuator chambers can be rounded, which would provide a more human-like appearance and functionality. In addition, as is discussed hereinbelow, the finger actuator can employ an embedded extensible fabric (in addition to or in lieu of thicker external walls) to limit radial expansion. Additional details on the manufacture and use of such actuator is found in application U.S. Ser. No. U.S.61/867,845, filed Aug. 20, 2013, which is incorporated in its entirety by reference.

Figure 3A:
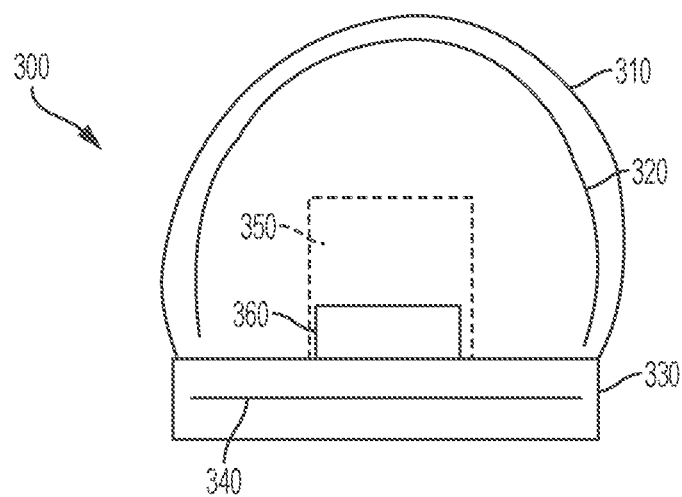
FIGS. 3A and 3B are schematic cross-sectional illustrations of a finger actua tor along the (A) lateral and (B) longitudinal dimension according to one or more embodiments.
Figure 3B:
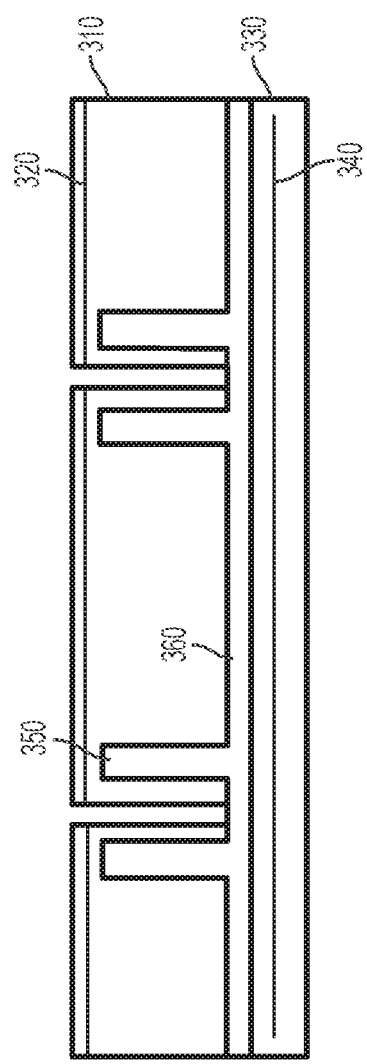

FIG. 3 is a schematic illustration of a finger actuator 300 according to one or more embodiments. FIG. 3A shows a lateral cross-sectional view of one segment in the finger actuator. FIG. 3B shows a lateral cross-sectional view of a plurality of segments in the finger actuator. The finger segment includes an upper elastomeric section 310 having an extensible layer 320 embedded therein. The elastomer can be a low stiffness silicone rubber elastomer such as EcoFlex silicone rubbers. EcoFlex rubber is very soft, very strong and very "stretchy", stretching many times its original size without tearing and will rebound to its original form without distortion. In one or more embodiments, an elastomer having an elongation at break of at least 500%, at least 800% and up to and including 1000% or even higher or any range bounded by the values recited herein can be used. They can have a tensile strength of greater than 100 psi, greater than 200 psi, greater than or equal to 350 psi or up to 500 psi or any range bounded by the values recited herein. The low stiffness and large extensibility enables the elastomer to expand to large volumes at relatively low pressures. Exemplary elastomers can have a Shore hardness of between 00-5 and A-100 or any range bounded by the values recited herein.

The upper elastomeric section 310 is secured to inelastic layer 330 having an inextensible sheet 340 embedded therein. The inelastic layer can be made of the same elastomeric polymer as the upper layer 310, with the additional stiffness arising from the incorporation of a reinforcing inextensible layer such as paper. In other embodiments, the inelastic layer 330 can be made of a stiffer elasomeric material, such as Elastosil silicone elastomer.

The upper elastomeric layer defines an open space 350 (shown in dashed lines to indicate that it is offset into the plane of the figure and within the chamber). The upper elastomeric layer also includes a channel 360 that runs along the length of the chamber and spans the distance between adjacent chambers. Channel 360 is in fluid connection with adjacent chambers and with an external port for pressurizing the chamber. Each finger segment includes an outer wall, e.g., a rounded outer wall that mimics a human finger) and an interior wall that faces an adjacent finger segment. The inner wall is free standing, in that it is not joined to adjacent finger segment, except at a base location where a channel fluidically connects the finger segments.

In one or more embodiments, the number of finger segment in the finger actuator is selected to mimic the joint movement of a hand. In one or more embodiments, the actuator contains 3-6 finger segments.

In one or more embodiments, the finger actuator includes additional layers of fabric embedded in each finger segment to prevent undesired radial expansion of the finger segment which may cause the actuator to break. The radial expansion of the actuator is constrained by application of a constraining fabric to the walls of the extensible elastomeric top layer. For example, an expandable fabric, such as a spandex fabric, layer or even an inextensible layer can be introduced around each actuation chamber exterior to control the expansion of these chambers individually. In other embodiments, the restraining fabric can be embedded in the elastomeric material making up the extensible chambers. Examples of extensible fabrics are spandex, polyamide, and elastane. Examples of inextensible fabrics are cotton, paper, polyester.

In one or more embodiments, the open space 350 within the actuators may be fabricated using a loss-wax approach, in which a wax mold of the internal structure of the actuator is placed within a mold during the curing of the elastomer. Subsequently the wax can be melted out of the actuator providing a void space for pressure to be supplied. See, e.g., FIG. 4C.

Fabrication of the figure actuator is described with reference to FIG. 4A-4D.

Figure 4A:
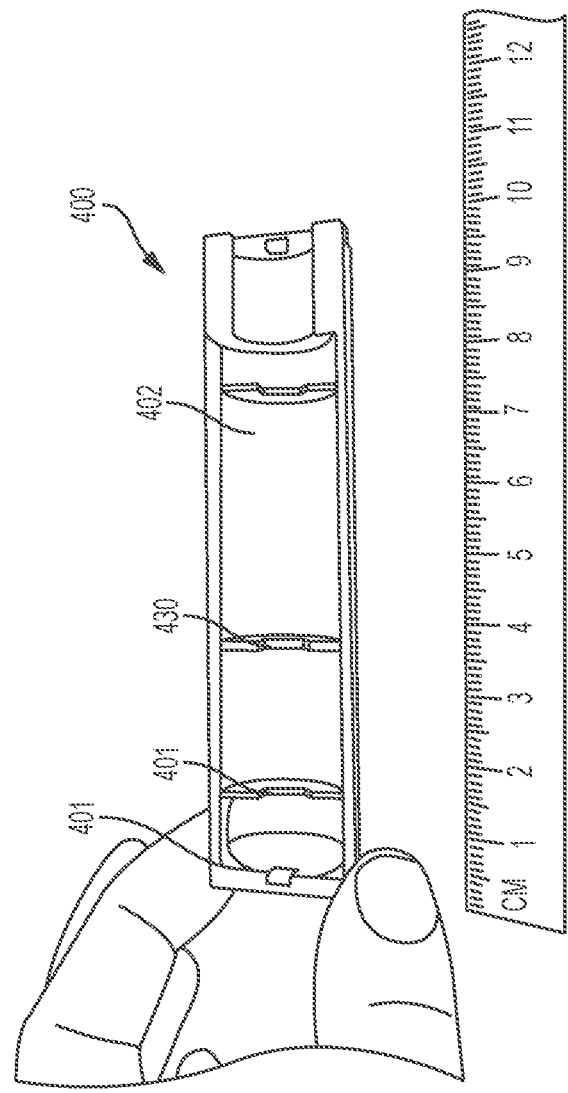
FIGS. 4A-4D are a series of photographs illustrating a fabrication process for a finger actuator according to one or more embodiments.

FIG. 4A is a photograph of the mold 400 used to manufacture the finger actuator. Mold 400 includes a base having a curved surface, mimicking a human finger. The interior of the mold includes spacers 430 that define the spacing between mold sections 402. The number of spacers can vary and is selected to provide the desired number of joints in the finger actuator. The spacers also include a recess 401 that are sized to accommodate wax mold 405. Similar recesses 401 can be located in the mold walls.

Figure 4B:
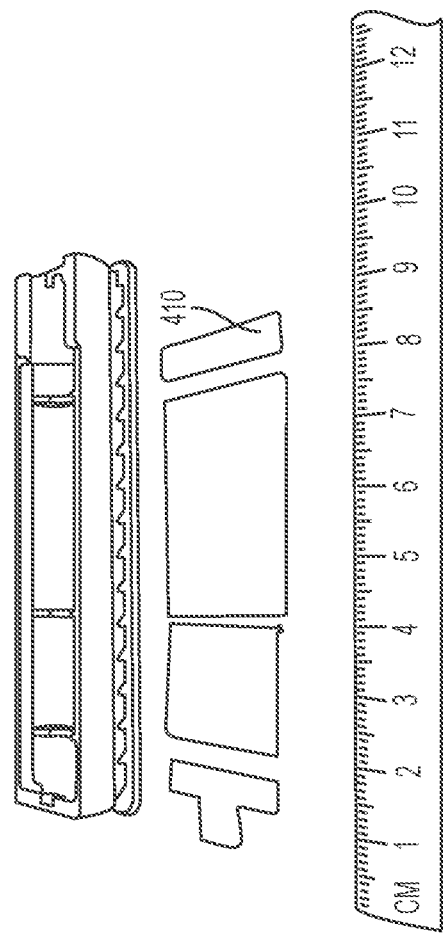

Next the reinforcing fabric is lined into the mold. Reinforcing extensible fabric 410 is provided, as shown in FIG. 4B. Each mold section 402 is provided with reinforcing fabric sized to fit. The fabric is inserted into the mold and pressed along the walls of the mold so that the fabric lines the mold inner surface.

Figure 4C:
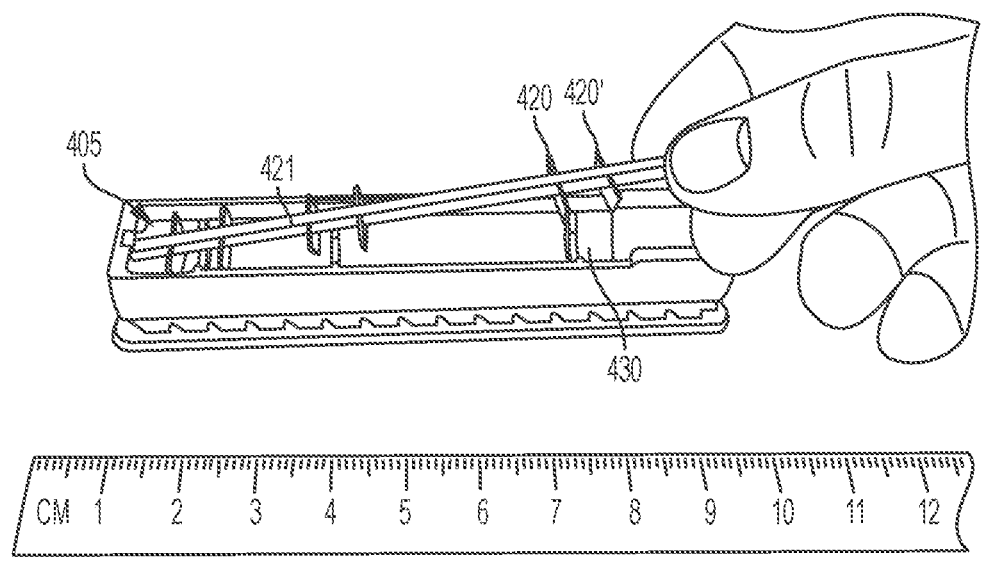

Next the wax internal structure is positioned within the mold. FIG. 4C is a photograph of an exemplary wax mold 405 including a supporting beam 421 (that runs along the length of the finger actuator's multiple segments and which forms the interconnected channel of the final actuator) and plates 420, 420' (shown here positioned proximate to one end of the finer segment and which forms the void spaces of the finger segment of the final product). FIG. 4C further illustrates the positioning of the lost wax mold 405 in a mold for manufacture of the finger actuator. Plates 420, 420' are positioned on either side of a spacer 430, which defines the 'joint' in the molded finger. The plates designate the void spaces of the finger actuator that will expand and induce the bending motion upon pressurization. A pair of plates 420, 420' are positioned proximate to and on opposite sides of spacer 430.

Figure 4D:
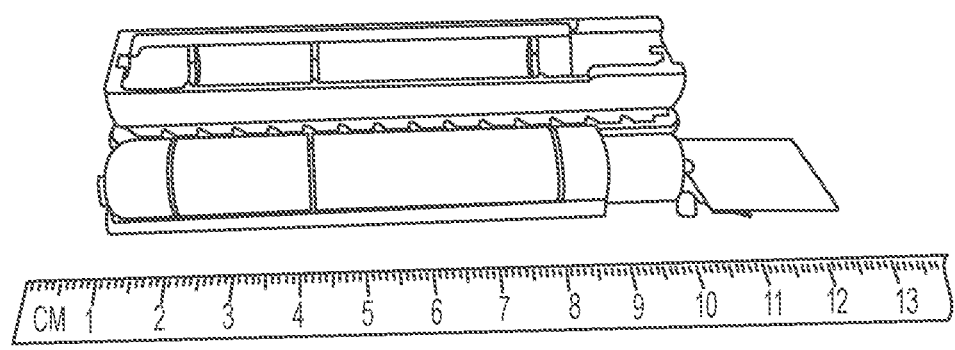

The mold is then filled with an elastomer precursor, such as EcoFlex silicone rubber and cured to produce a hardened body. The inelastic base layer having an inextensible sheet embedded therein can be formed integrally with the chambers, by pressing a final inextensible sheet into the filled mold prior to curing. In this case, the base and the chambers are made of the same elastomeric polymer. In other embodiments, the inelastic base can be joined to the molded chambers after curing. For example, a polymer layer having an inextensible sheet embedded therein can be bonded to the molded chambers using a curable silicone elastomer as adhesive. FIG. 4D is a photograph of the molded finger actuator after removal from the mold.

After the elastomer is cured, the molded actuator is heated to melt the wax from the lost wax mold and create the voids and channel interconnects of the actuator.

Figure 5:
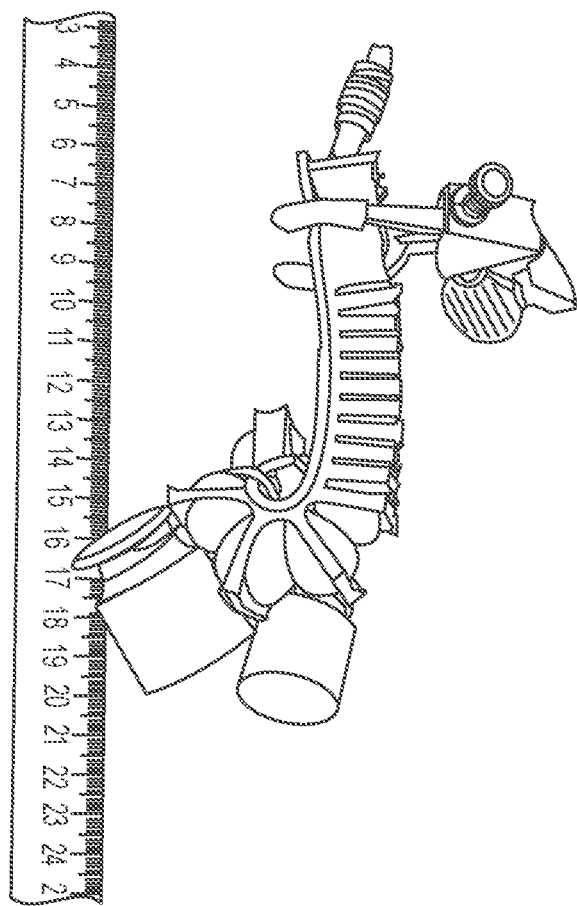
FIG. 5 illustrates the experiment used to test the strength of the actuators.

FIG. 5 shows a picture of an experiment used to test the strength of the actuators. This experiment was used to obtain the data shown in FIG. 6. The actuators were individually tested (separate from the body of the hand and separate from the portable control system). They were mounted at one end and pressurized (so they would bend), and various weights were suspended from the actuators. The pressure at which the actuator could no longer hold a given weight was recorded and plotted. The data in FIG. 6 show the weight an actuator could hold (just like a finger holding a weight) and the pressure required to hold that weight.

Three different actuators were evaluated.

Figure 6:
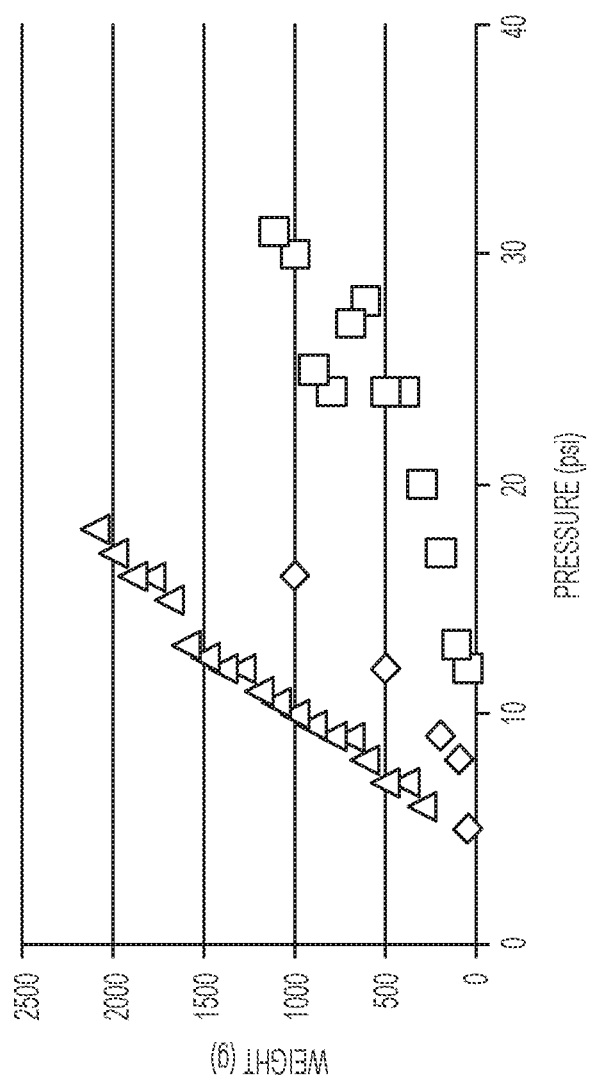
FIG. 6 is a plot of weight (g) v. pressure (psi) for a finger actuator according to one or more embodiments of the invention and for two comparison actuators.

A finger actuator reported in FIG. 6 as a series of round shaped data points corresponds with a pneumatic actuator as described in FIGS. 3 and 4. The actuator is prepared using an EcoFlex silicone elastomer, a spandex extensible reinforcing material for the chambers and a paper inextensible reinforcing material for the base.

Comparison actuator #1 is reported in FIG. 6 as a series of diamond shaped data points. Comparison actuator #1 corresponds to a pneumatic actuator having the structure shown in FIG. 2 having a rectangular cross-sectional geometry, in which the outer walls are thicker than the inner walls and are not reinforced with an extensible material. The actuator is prepared using an Elastosil silicone elastomer, which is a stiffer elastomer than EcoFlex silicone rubber.

Comparison actuator #2 is reported in FIG. 6 as a series of square shaped data points. Comparison actuator #2 corresponds to a pneumatic actuator having a rounded shape with three joints (similar to the finger actuator), with the following differences. Comparison actuator #2 is made from an Elastosil silicone elastomer, which is a stiffer elastomer than EcoFlex silicone rubber. In addition, a spandex fabric layer was sewn around the exterior of the actuator to control the expansion of the chambers.

The data show that the finger recent actuator can hold more weight with less pressure compared to the design s of Comparison actuators #1 and #2, which means that the actuator is better suited for portable prosthetic devices limited to small air compressors that can generate small pressures.

Prosthetic Hand

In one or more embodiments, the finger actuator is secured to a hand base to provide a prosthetic hand. The finger actuator is secured using metal screws that immobilize a 3D printed holder for the fingers to the hand base. Other methods of securing the finger actuator are contemplated.

Control System

A microprocessor controlled compressor controls the pressurization of the finger actuators. In use, a pneumatic manifold system can be employed which would allow for a number of finger positions to be generated with the same single pressurized air input. In one or more embodiments, the user (e.g., an upper limb amputee) wears a myoelectric sensor which detects muscle movements in their upper arm, causing the compressors to turn on/off. Myoeletric sensors work by sensing, using electrodes when the muscles in the upper arm move, causing an artificial hand to open or close. Other methods for providing signal input to the actuators is contemplated.

In addition, pneumatic manifolds can be used to obtain certain combinations of actuation of the fingers for the prosthetic hand. This strategy will greatly reduce the complexity of controlling the prosthetic hand compared to controlling each finger individually. Additional detail on pneumatic manifolds is found in co-pending application PCT/US13/66164, filed Oct. 22, 2013, the contents of which are incorporated entirely by reference.

For demonstration purpose herein, the control system is designed for a user to flip a switch to turn on or off the air compressors which are powered by a battery.

Figure 7:
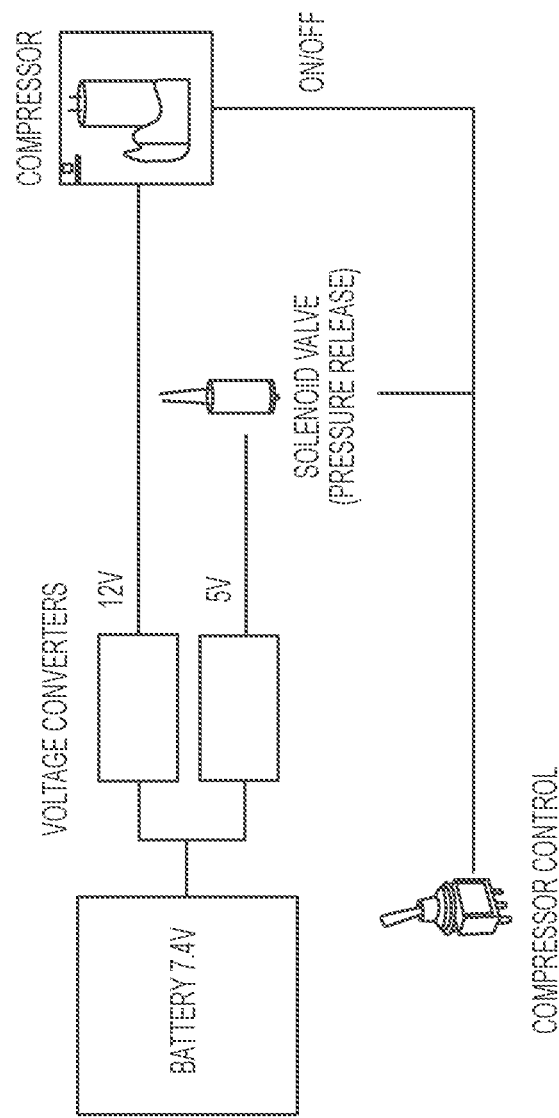
FIG. 7 is a schematic illustration of the control system of a robotic hand according to one or more embodiments.
Figure 8:
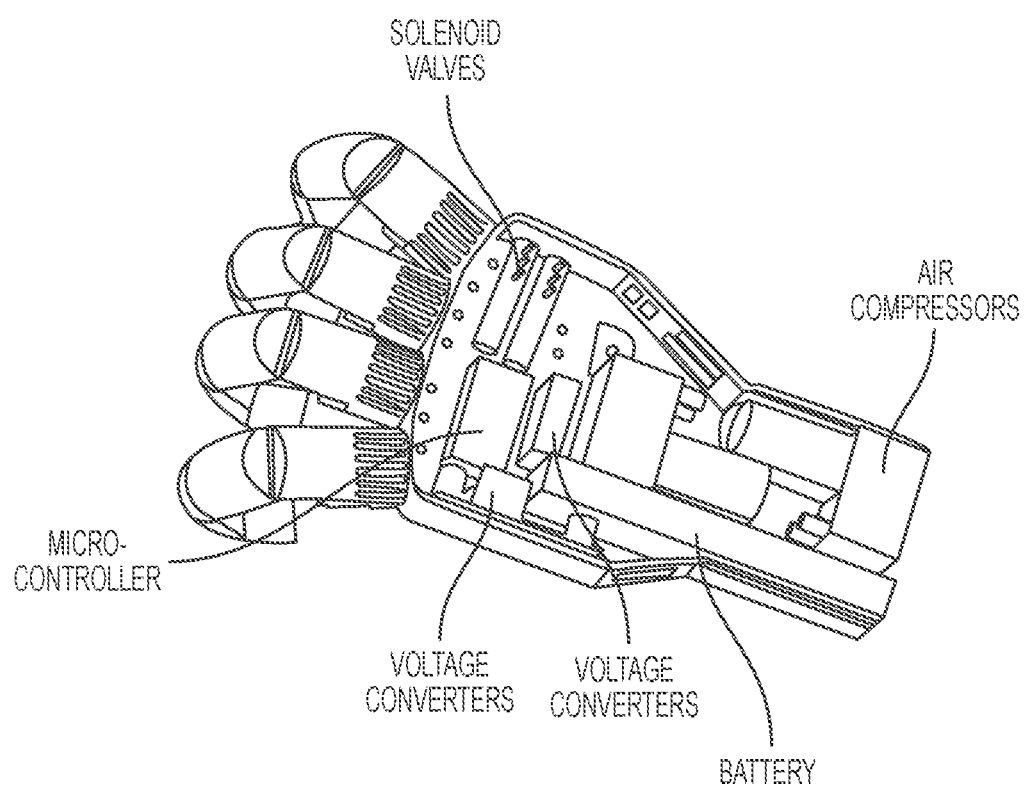
FIG. 8 is a schematic illustration of a prosthetic hand including control system according to one or more embodiments.

Description of various control system components is provided with reference to FIGS. 7 and 8. The components can be housed in a sleeve connected to the hand base or can be integrated, in whole or in part, into the hand base.
1) Battery: Rechargeable lithium battery provides mobile power supply
2) Voltage converters: Two commercially-available voltage converter chips take in the 7.4-volt battery power supply and generate one 9-volt output and one 5-volt output to power other components described below.
3) Air compressors: Two air compressors are controlled by a small slide switch (not shown) which allows the user to turn them on or off. The compressors take in air from the atmosphere and pressurize it, sending it through tubing to the solenoid valves.
4) Solenoid valves: The solenoid valves open or close the tubing connecting the air compressors with the actuators. The user can open the valve using a second electrical switch (separate from the compressors). If the valve is open and the compressors are turned on, the fingers will inflate. If the valve is closed, the air will be blocked from entering or exiting the actuators.
5) Microcontroller: The microcontroller is used to control the solenoid valves by reading a myoelectric sensor which will read muscle voltage from the amputee. If the user flexes their muscle, the microcontroller will read the signal and open the solenoid valve/turn on the air compressors (thus causing the fingers to bend). Additional methods for providing input to the prosthesis are also contemplated.

The fully functional prosthesis can be worn by a user with an upper limb amputation. Myoelectric sensors placed on the upper arm or back muscles can determine when the amputee flexes their muscles. The signal can be sent to the microcontroller which then turns on the air compressors and opens the solenoid valves. Various muscle flexing patterns result in opening various combinations of solenoid valves (thus resulting in different hand grip configurations). The user can recharge the battery as needed.

As will be apparent to one of ordinary skill in the art from a reading of this disclosure, the disclosed subject matter can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

It is noted that one or more publications, patent application, patents, or other references are incorporated herein. To the extent that any of the incorporated material is inconsistent with the present disclosure, the present disclosure shall control.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention.

What is claimed is:

1. A finger actuator, comprising:
a plurality of fluidically interconnected extensible segments, wherein:
   each extensible segment comprises two inner walls at opposing ends of the extensible segments that allow expansion of the extensible segment in the lateral direction and an outer wall that is thicker than the inner walls to prevent radial expansion of the extensible segment; and
   each extensible segment comprises two fluidically connected inflatable chambers located proximate to the inner walls; and
an inextensible layer connected to the plurality of fluidically interconnected extensible segments at a base of the extensible segments, the inextensible layer comprising a flexible layer and an inextensible material that extends along the length of the plurality of fluidically interconnected extensible segments.

2. The finger actuator of claim 1, wherein the plurality of extensible segments comprises 3-6 segments.

3. The finger actuator of claim 1, wherein the finger actuator further comprises a hinge integrally molded with the fluidically interconnected extensible segments.

4. The finger actuator of claim 3, wherein the hinge is connected to the inextensible layer to form a flexible, inextensible hinge.

5. The finger actuator of claim 1, wherein the extensible segments are comprised of a silicone rubber.

6. The finger actuator of claim 1, wherein the inextensible material comprises cotton, paper, or polyester layers.

7. The finger actuator of claim 1, wherein the flexible layer of the inextensible layer is comprised of the same material as the extensible segments.

8. The finger actuator of claim 1 wherein the flexible layer of the inextensible layer is comprised of a different material than the extensible segments.

9. The finger actuator of claim 1, wherein the two fluidically interconnected chambers are molded.

10. The finger actuator of claim 1, further comprising a hand base, wherein the finger actuator is secured to the hand base at one end of the finger actuator.

11. The finger actuator of claim 10, wherein the hand base comprises an air compressor, the air compressor fluidically connected to the secured finger actuator.

12. The finger actuator of claim 11, further comprising a valve for reversibly connecting the air compressor to the secured finger actuator.

13. The finger actuator of claim 12, wherein the hand base further houses a microprocessor for receiving input from a sensor and transmitting instructions to open or close the valve in response to the input.

14. A method of operating a finger actuator comprising:
providing a first finger actuator secured to a hand base, wherein the finger actuator comprises:
a plurality of fluidically interconnected extensible segments, wherein
   each extensible segment comprises two inner walls at opposing ends of the extensible segments that allow expansion of the extensible segment in the lateral direction and an outer wall that is thicker than the inner walls to prevent radial expansion of the extensible segment, and
   each extensible segment comprises two fluidically connected inflatable chambers located proximate to the inner walls; and
an inextensible layer connected to the plurality of fluidically interconnected extensible segments at a base of the extensible segments, the inextensible layer comprising a flexible layer having an inextensible material that extends along the length of the plurality of fluidically interconnected extensible segments; and
providing instructions to a valve housed in the hand base to open, wherein air pressure from an air compressor housed in the hand base pressurizes at least one finger actuator, thereby causing the finger actuator to bend.

15. The method of claim 14, wherein the instruction is in response to a signal received from a sensor.

16. The method of claim 14, further comprising a second finger actuator located at a position of the hand base spaced apart and opposed to the first finger actuator.

17. The method of claim 16, wherein the first finger actuator and the second finger actuator are pressurized and the combined pressurization of the first finger actuator and the second finger actuator provides a gripping motion.

* * * * *